(12) United States Patent
Eberhard et al.

(10) Patent No.: US 7,247,754 B2
(45) Date of Patent: Jul. 24, 2007

(54) METHOD FOR THE PRODUCTION OF TRIMERIC KETONE PEROXIDE SOLUTIONS

(75) Inventors: Hägel Eberhard, Icking (DE); Appel Hans, Pullach (DE)

(73) Assignee: Degussa Initiators GmbH & Co. KG., Pullach (DE)

( * ) Notice: Subject to any disclaimer, the term of this patent is extended or adjusted under 35 U.S.C. 154(b) by 59 days.

(21) Appl. No.: 10/546,940

(22) PCT Filed: Feb. 26, 2004

(86) PCT No.: PCT/EP2004/001920

§ 371 (c)(1),
(2), (4) Date: Aug. 25, 2005

(87) PCT Pub. No.: WO2004/076405

PCT Pub. Date: Sep. 10, 2004

(65) Prior Publication Data

US 2006/0211872 A1 Sep. 21, 2006

(30) Foreign Application Priority Data

Feb. 28, 2003 (DE) ................................ 103 08 891

(51) Int. Cl.
*C07C 49/00* (2006.01)
*C07C 409/00* (2006.01)
*C07D 321/00* (2006.01)

(52) U.S. Cl. ...................... 568/368; 568/373; 568/568; 549/267

(58) Field of Classification Search ..................... None
See application file for complete search history.

(56) References Cited

U.S. PATENT DOCUMENTS

| 2,909,513 A | 10/1959 | Overbaugh |
| 3,781,303 A | 12/1973 | Busch et al. |
| 3,925,417 A | 12/1975 | Story et al. |

FOREIGN PATENT DOCUMENTS

| DE | 44 38 147 A | 5/1996 |
| GB | 827 511 A | 2/1960 |
| GB | 873 614 A | 7/1961 |
| GB | 912 061 A | 12/1962 |
| GB | 998 686 A | 7/1965 |
| GB | 1 108 871 A | 4/1968 |
| GB | 1 462 854 A | 1/1977 |

OTHER PUBLICATIONS

Synthesis of Hexadecanolide, Harding, et al. Ind. Eng. Chem., Prod. Res. Dev., (1975).

*Primary Examiner*—Sikarl A. Witherspoon
(74) *Attorney, Agent, or Firm*—Fulbright & Jaworski L.L.P.

(57) ABSTRACT

Cyclohexane is reacted with hydrogen peroxide in the presence of nitric acid which is used as a catalyst in a suitable solvent for the production of trimeric cyclohexane peroxide.

10 Claims, 1 Drawing Sheet

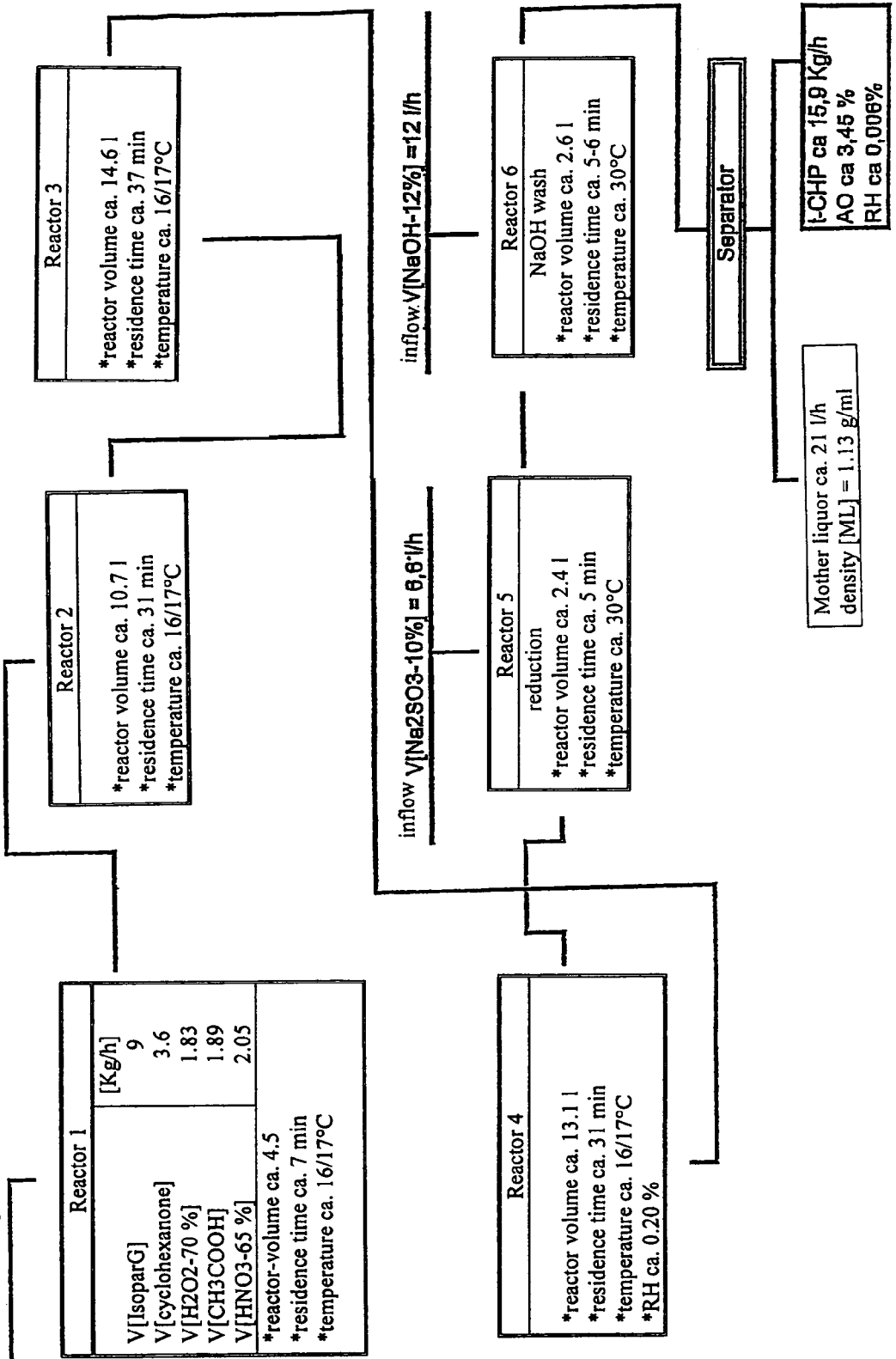

METHOD FOR THE PRODUCTION OF TRIMERIC KETONE PEROXIDE SOLUTIONS

BACKGROUND AND SUMMARY OF THE INVENTION

This is a §371 of PCT/EP2004/001920 filed Feb. 26, 2004, which claims priority from German Patent Application No. 103 08 891.1 filed Feb. 28, 2003.

Trimeric cyclic ketone peroxides are known. In 1968 P. Story (JACS 90, 817 (1968)) discovered a method for producing macrocyclic hydrocarbons and lactones from tricycloalkylidene peroxides by pyrolysis. Hence tricycloalkylidene peroxides are valuable starting materials for preparing these classes of compounds which are otherwise very difficult to produce.

Tricyclohexylidene peroxide (trimeric, cyclic cyclohexanone peroxide) is particularly in demand for the synthesis of cyclopentadecane and hexadecanolide which are starting materials for musk perfumes.

In DE 21 32 616 P. Story discloses a two-step method for producing tricyclo-alkylidene peroxides. He prepares a 1-hydroperoxy-1'-hydroxy-dicycloalkylidene peroxide from cycloalkanone, hydrogen peroxide and acid and converts it further with strong acids to form the desired cyclic compound. Trimers and dimers are formed in this process approximately in a ratio of 75:25 in yields of <60% based on the cycloalkanone that was used.

The handling of these solid peroxides which are very sensitive to friction and shock is a safety risk.

Harding and Whalen (Industrial and Engineering Chemistry, Product Research Development 1975, vol. 14, No. 4, p. 232-239) published a study on the preparation of trimeric, cyclic cyclohexanone peroxide and investigated the direct preparation of cyclohexanone and hydrogen peroxide without isolating open-chain intermediate products. They were able to avoid the risk of handling solid peroxides by working in solvents (high-boiling hydrocarbons). They optimized the conditions of synthesis (type and amount of solvent, acid and temperature) in extensive experiments. Under the best conditions they obtained trimeric cyclic cyclohexanone peroxide in a yield of 84% in addition to 1 to 7% and on average 4% dimers. The reaction time at about 20° C. was 22 hours. The most suitable acids proved to be 70% perchloric acid and concentrated hydrochloric acid. The use of sulfuric acid resulted in substantially longer reaction times.

They strongly advised against the use of nitric acid because of the danger of forming unstable pernitric acid.

The disadvantages of this method are the use of 70% perchloric acid (dangerous, expensive) or concentrated hydrochloric acid (corrosive; chlorine can be formed with hydrogen peroxide), the use of a large quantity of acetic acid as a solubilizer (250 g/mol cyclohexanone, waste water pollution!) and the long reaction time which makes a batch process uneconomical and makes it practically impossible to carry out a continuous process.

Hence there is a need to create a method for producing trimeric ketone peroxides which as selectively as possible (without large amounts of dimers) results in a high yield, a short reaction time and as little waste as possible and also enables a continuous operation.

Hence the object of the invention is to create a method which has the stated advantages.

This is achieved according to the invention by a method for producing trimeric ketone peroxides by reacting cyclic or open-chain ketones with $H_2O_2$ in the presence of an acidic catalyst in a suitable solvent which is characterized in that nitric acid is used as the catalyst.

BRIEF DESCRIPTION OF THE DRAWING

The Drawing is a flow chart of a process according to the present invention.

DETAILED DESCRIPTION

Surprisingly it was found, that contrary to the teaching of Harding and Whalen, the use of nitric acid is not associated with any safety risk whatsoever and that, even more surprisingly, the use of nitric acid increases the reaction rate to such an extent that the reaction is already completed after 1 to 2 hours instead of in more than 20 hours. The desired trimers are formed in a yield of about 90% and the ratio of trimer: dimer is 94:6 at reaction temperatures of about 15° C.

Those with 5 to 12 chain links are used as cyclic ketones. The cyclic ketones can be substituted with one or more alkyl groups having 1 to 6 C atoms. The open-chain ketones that come into consideration have the formula $R^1$—CO—$R^2$ in which $R^1$ and $R^2$ each independently of one another can contain 1 to 15 carbon atoms in the chain such that $R^1+R^2$ can have a maximum value of 30 and a minimum value of 2. The chains can in turn be substituted with alkyl groups of 1 to 6 C atoms. Preferred cyclic ketones are cyclohexanone as well as cyclohexanone substituted with 1, 2 or 3 alkyl groups having 1 to 6 C atoms as well as cyclopentanone. Examples of suitable cyclic ketones of the preferred group are 3,3,5-trimethylcyclohexanone, 2-methylcyclohexanone, 4-methylcyclohexanone and 4-tert.-butylcyclohexanone. Cyclododecanone has also proven to be suitable. Among the alicyclic ketones methyl ethyl ketone and acetone are particularly preferred. Other preferred ketones are those in which $R^1$ or/and $R^2$ has 1 to 4 straight-chain or branched C-atoms, is in particular a tert.-butyl group.

The nitric acid is expediently used in a concentrated form, preferably as a 60 to 75% solution. The amount is expediently 0.3 to 0.7 mole, preferably 0.4 to 0.6 mole per mole cyclohexanone.

Liquid hydrocarbons are suitable as the solvent and in particular those having 6 to about 20 C atoms which can be linear or branched. Examples of suitable solvents are isododecane and the hydrocarbons distributed under the trade names Shellsol T, Isopar M, G and E as well as aromatic compounds such as toluene, xylene and phthalate ester. Diesel fuel is suitable as a solvent especially for trimeric methyl ethyl ketone peroxide (MEKP) and trimeric acetone peroxide (AP). The said solvents have a desensitizing effect and reduce the risk of explosion of the pure peroxides. For desensitization it is also possible to use solid desensitizers such as phthalates, and fillers such as chalk, kaolin and silicic acid and in particular dicyclo-hexyl phthalate.

The crystallization of the cyclic trimeric ketone peroxides in pure form can be avoided by using non-polar hydrocarbons as a solvent which is advantageous for safety. For this purpose isoalkanes, e.g. Isopar G, have proven to be particularly useful.

As mentioned above acetic acid is preferably used in the method of the invention as a solubilizer. Depending on the selected reaction conditions, 30 to 100 g acetic acid per mole ketone achieves the best results in this method.

According to the invention the amount of acetic acid which is preferably used as a solubilizer could be reduced by 80% compared to the method of Harding and Whalen (from 250 g to 50 g/mole ketone). This is an important economic factor and reduces the pollution of the waste water with organic substances. However, instead of acetic acid or in addition thereto, it is also possible to use other substances as a solubilizer such as propionic acid, acetonitrile, lower alcohols such as methanol and mixtures thereof.

At the end of the reaction according to the invention which, as already mentioned, is expediently carried out in an aliphatic hydrocarbon, e.g. Isopar G, while stirring and cooling, a two-phase mixture is formed after completion of the stirring. The desired reaction product is present in solution in the organic phase and non-reacted starting products and by-products are present in the aqueous phase. The organic solution can be used directly for further reactions or the trimeric ketone peroxide can be isolated therefrom as a solid.

Another hazard in the prior methods was that in the aqueous phase separated after the reaction which still contains ketone, hydrogen peroxide, open-chain ketone peroxides and the entire acid, the dimer can readily form when allowed to stand which can precipitate as an insoluble solid and can explosively decompose when mechanically stressed.

According to a preferred embodiment of the method according to the invention the entire reaction mixture is treated with a sodium sulfite solution at the end of the reaction, resulting in reduction of $H_2O_2$ and all hydroperoxides. Hence no secondary reaction can occur after the phase separation.

The hydrogen peroxide is expediently used in a concentrated commercial form i.e. as an approximately 60 to 80% aqueous solution. Commercial 70% $H_2O_2$ is particularly suitable.

The reaction temperature is kept in the range of 10 to 25° C., preferably in the range of 15 to 20° C. The reaction runs to completion in 1 to 3 hours in this preferred temperature range.

Due to this short reaction period, the method according to the invention can also be carried out continuously with very good results. For a continuous operation it is expedient to use several successive reaction vessels or containers. The reaction time required for the quantitative reaction, which as mentioned above, is 1 to 3 hours, preferably 1.5 to 2 hours is achieved in the continuous process by appropriately matching the number and size of the various reaction vessels to the flow rate. An example of continuous operation of the method according to the invention using 6 reaction containers is shown in FIG. 1 of the attached drawing. The number of reaction containers, their size and the residence times can of course be altered and adapted to the respective given conditions as is readily apparent to a person skilled in the art.

The solutions of trimeric ketone peroxides obtained according to the invention or the solid products obtained therefrom are particularly suitable for polymerizing monomers, for heat-curing unsaturated polyester resins, for degrading polypropylene (PP), as a diesel additive to improve the cetane number and to reduce soot formation (in particular trimeric MEKP and AP). Furthermore, the corresponding dimeric ketone peroxides can be obtained from the solutions obtained according to the invention by heating the organic solution to 25 to 50° C. in the presence of desensitizers which reduces the risk of explosion of the dimers that precipitate during heating to an acceptable level. Dimeric ketone peroxides prepared in this manner and in particular dimeric cyclohexanone peroxide can be used to produce caprolactam or anti-malaria agents.

The invention is further elucidated by the following examples.

EXAMPLE 1

Batch process for producing a solution of trimeric cyclohexanone peroxide (CHP)

300 g (3.06 mol) cyclohexanone, 150 g acetic acid and 1000 g Isopar G (an iso-alkane) are placed first in a 2 l reactor and cooled to +15° C. During approximately 15 minutes, 150 g (3.09 mol) 70% $H_2O_2$ is added while stirring and cooling during which the temperature is kept below +20° C. Subsequently 135 g (1.39 mol) 65% nitric acid is added within 25-30 minutes while cooling well. It is stirred for 1.5 hours at 15-18° C., then a solution of 40 g (0.15 mol) $Na_2SO_3$ in 360 g water is added within 5 minutes and the temperature is allowed to increase to 30° C. It is stirred for a further 10 minutes, the stirrer is stopped and the aqueous phase is separated after 10 minutes (780 g).

The organic phase is washed with 500 ml 8% sodium hydroxide solution and twice with 500 ml water in each case.

1280 g of a colourless solution is obtained having a content of 24.3% trimeric cyclic cyclohexanone peroxide corresponding to 89.1% of theory and 1.5% content of dimeric, cyclic cyclohexanone peroxide dissolved in Isopar G.

EXAMPLE 2

Continuous Process

The trimeric cyclohexanone peroxide (t-CHP) is synthesized in a reaction cascade as shown in the drawing. In addition, cyclohexanone, hydrogen peroxide, nitric acid, acetic acid and/or Isopar G were fed simultaneously into reactor 1 and kept there while stirring and cooling to 15° C. At this temperature the trimeric CHP is mainly formed under the catalytic influence of nitric acid. The subsequent reactors 2, 3 and 4 having the same reaction temperature are used for the secondary reaction. The corresponding dimeric cyclohexanone peroxide and open-chain hydroperoxide-containing CHP are formed as by-products.

The interfering hydroperoxide groups are reduced in reactor 5 with sodium sulfite. The acid which is still present in the reaction solution is neutralized with sodium hydroxide solution in reactor 6 and separated with the aqueous phase by separation with a separator.

In contrast to the batch process of example 1, nitric acid, Isopar G, acetic acid and hydrogen peroxide are simultaneously added with the cyclohexanone, the reaction mixture is reduced without separating the mother liquor, and neutralized. Also somewhat more nitric acid is used. The AO yield increases from about 89% to about 93%. Moreover it is possible to use a higher concentration.

EXAMPLE 3

Preparation of the Trimeric Methyl Ethyl Ketone Peroxide (MEKP)

Methyl ethyl ketone (350 g), isododecane (400 g) and glacial acetic acid (320 g) are added first. 65% (215 g) nitric acid is added at 15 to 18° C. Then 70% (240 g) hydrogen peroxide is added dropwise at 14-18° C. and it is stirred for a further hour. The aqueous phase is separated.

The organic phase is reduced with sodium sulfite solution and washed with dilute sodium hydroxide solution and subsequently with water.

Yield: 716 g (75.4%)

Content: 41% Trimeric Cyclic MEKP 4% dimeric cyclic MEKP

EXAMPLE 4

Preparation of the Dimeric Cyclic Cyclohexanone Peroxide

The synthesis is carried out in two stages: Firstly the trimeric cyclic cyclohexanone peroxide (tCHP) is prepared. The product is not isolated and is converted in the second step into pure dCHP.

Trimeric cyclic cyclohexanone peroxide in isododecane.

Cyclohexanone (240 g), glacial acetic acid (240 g) and isododecane (800 g) are added first and 70% (120 g) hydrogen peroxide is slowly added at 18° C. Then nitric acid (110 g) is added dropwise at 18° C. It is stirred for a further hour at 18° C.

It is reduced with sodium sulfite solution and washed with dilute sodium hydroxide solution. Subsequently it is washed with water. The solution is directly converted into dCHP.

Yield: 1038 g; tCHP content of the solution: ca. 21%
Dimeric cyclic cyclohexanone peroxide Glacial acetic acid (100 g) is added to a solution of the tCHP in isododecane. Nitric acid (85 g) is added dropwise at 30° C. and it is stirred for a further two hours at 40° C. Then it is cooled down to 25° C., water is added and the precipitate that is formed is filtered. The product is washed with water.

Yield: 175 g water-moist (ca. 90%) dCHP; GC-content: 99%.

The invention claimed is:

1. A method for producing trimeric cyclic ketone peroxides comprising reacting a ketone with hydrogen peroxide in the presence of an acidic catalyst and acetic acid as the solubilizer in a suitable solvent, wherein nitric acid is the acidic catalyst.

2. A method claimed in claim 1, wherein said solvent is a non-polar hydrocarbon or a mixture thereof.

3. A method a claimed in claim 1, wherein acetic acid is used in an amount of 30 to 100 g/mol ketone.

4. A method as claimed in claim 1, wherein said ketone is a cyclic ketone with 5 to 12 chain links which can be substituted with one or more alkyl groups having into 6 carbon atoms or an alicyclic ketone of the formula $R^1$—CO—$R^2$, in which $R^1$ and $R^2$ each independently of one another can contain 1 to 15 carbon atoms in the chain and the chains can be substituted by alkyl groups having 1 to 6 carbon atoms.

5. A method as claimed in claim 1, wherein the reaction is carried out in a temperature range of 1 to 25° C.

6. A method as claimed in claim 1, wherein 60 to 80% hydrogen peroxide is present.

7. A method as claimed in claim 1, wherein the reaction is carried out within 2 to 3 hours at a temperature of from 10 to 20° C.

8. A method as claimed in claim 1, wherein the reaction is carried out continuously using several successive reaction vessels in which the total residence time of the reaction mixture is 1 to 3 hours.

9. A method as claimed in claim 1, wherein hydroperoxy groups are removed by adding sulfite after completion of the reaction.

10. A method as chimed in claim 1, wherein nitric acid and glacial acetic acid are again added to the resulting solution of the trimeric ketone peroxide, heated to >25° C. to 50° C. and dimeric ketone peroxide is isolated.

* * * * *